(12) United States Patent
Mollenhauer et al.

(10) Patent No.: US 10,500,154 B2
(45) Date of Patent: Dec. 10, 2019

(54) INJECTABLE BIOCOMPATIBLE COMPOSITION

(75) Inventors: Juergen Mollenhauer, Reutlingen (DE); Karin Benz, Goeppingen (DE); Barbara Platz, Zornheim (DE); Helmut Wurst, Pfullingen (DE); Reinout Stoop, Voorschoten (NL)

(73) Assignee: NMI NATURWISSENSCHAFTLICHES UND MEDIZINISCHES INSTITUT AN DER UNIVERSITAET TUEBINGEN, Reutlingen (DE)

( * ) Notice: Subject to any disclaimer, the term of this patent is extended or adjusted under 35 U.S.C. 154(b) by 604 days.

(21) Appl. No.: 12/844,750

(22) Filed: Jul. 27, 2010

(65) Prior Publication Data

US 2010/0322993 A1 Dec. 23, 2010

Related U.S. Application Data

(63) Continuation of application No. PCT/EP2009/000542, filed on Jan. 28, 2009.

(30) Foreign Application Priority Data

Jan. 28, 2008 (DE) .................. 10 2008 008 071

(51) Int. Cl.
*A61K 9/00* (2006.01)

(52) U.S. Cl.
CPC ................. *A61K 9/0024* (2013.01)

(58) Field of Classification Search
None
See application file for complete search history.

(56) References Cited

U.S. PATENT DOCUMENTS

| | | | | |
|---|---|---|---|---|
| 5,750,585 | A * | 5/1998 | Park et al. | 521/143 |
| 2002/0032463 | A1 | 3/2002 | Cruise et al. | |
| 2002/0049498 | A1* | 4/2002 | Yuksel et al. | 623/17.16 |
| 2002/0193812 | A1* | 12/2002 | Patel | A61B 17/12022 606/151 |
| 2003/0040760 | A1 | 2/2003 | Hnojewyj et al. | |
| 2006/0089719 | A1 | 4/2006 | Trieu | |
| 2006/0255503 | A1* | 11/2006 | Higham et al. | 264/255 |
| 2010/0184223 | A1 | 7/2010 | Wurst | |

FOREIGN PATENT DOCUMENTS

| | | |
|---|---|---|
| EP | 1 263 327 | 8/2005 |
| WO | WO 99/07416 | 2/1999 |
| WO | WO 00/37124 | 6/2000 |
| WO | WO 01/60335 A2 | 8/2001 |
| WO | WO 01/60335 A3 | 8/2001 |
| WO | WO 01/66017 | 9/2001 |
| WO | WO 2009/010232 | 1/2009 |

OTHER PUBLICATIONS

Shalaby et al., ACS symposium series, 1991, p. 484-492.*
Ganey et al., Spine, 2003, 28: 2609-2620.*
Kawasaki et al., J. Cell. Physiol., 1999, 179: 142-148.*
Nie et al., J. Control Release, 2007, 122: 1-21.*
International Search Report dated May 19, 2009, from International Patent Application No. PCT/EP2009/000542.
Anseth et al., "In situ forming degradable networks and their application in tissue engineering and drug delivery," *Journal of Controlled Release* 78:199-209, 2002.

* cited by examiner

*Primary Examiner* — Ileana Popa
(74) *Attorney, Agent, or Firm* — Klarquist Sparkman, LLP

(57) ABSTRACT

The invention relates to an injectable biocompatible composition based on a polymeric support as well as to a method for producing it, which composition which comprises at least one hydrophilic polymer, wherein the polymer is polymerizable in situ to form a gel, and wherein the hydrophilic polymer is crosslinkable serum albumin or crosslinkable serum protein. The composition can be used in the restoration, the reconstruction, and/or the replacement of tissues and/or organs, or as a drug release implant in mammals. The composition is particularly suitable for treating cartilage disorders of a diseased or injured articular site in a mammal.

9 Claims, 1 Drawing Sheet

INJECTABLE BIOCOMPATIBLE COMPOSITION

CROSS-REFERENCES TO RELATED APPLICATIONS

This application is a continuation of international patent application PCT/EP2009/000542, filed on Jan. 28, 2009 designating the U.S., which international patent application has been published in German language and claims priority from German patent application DE 10 2008 008 07.3, filed on Jan. 28, 2008. The entire contents of these priority applications are incorporated herein by reference.

BACKGROUND OF THE INVENTION

The present invention relates to an injectable biocompatible composition based on a polymeric support which comprises at least one hydrophilic polymer, wherein the polymer is polymerizable in situ, and also to the use of this composition in medicine, and a process for its preparation.

Such injectable biocompatible compositions are used, inter alia, in the sector of medicine or surgery for the purpose of replacing or supporting degenerated or injured tissue, for example, cartilage tissue, of a patient. Particularly the field of restoration of articular cartilage currently makes use of such compositions with which substances such as pharmacologically active ingredients, hormones, enzymes, etc., but also cells, can be provided directly in situ at the site to be treated, so that the bioavailability of such substances or of the cells is made possible in the first place or increased. Such compositions are currently used, in particular, in the field of cartilage regeneration.

In order to be able to embed cells in biocompatible, tissue-forming matrices, such as, for example, hydrogels, essentially two conditions must be observed: gelification must not be inhibited by the presence of cells, and the vitality of the cells must not be impaired by gelification. These prerequisites must be taken into consideration both for the selection of the materials used and for the crosslinking reaction.

Hitherto, cells have been embedded in a series of synthetic polymers, such as, for example, polyethylene glycol, polyvinyl alcohol, etc., or natural polymers, such as, for example, agarose, alginate, chitosan, collagen, hyaluronic acid, fibrin, etc. Gel formation in synthetic polymers can take place through a chemical reaction, and also through self-association, or—as is the case with certain peptide sequences—through addition of salt, or through an increase in temperature. Naturally occurring polymers also often form gels through self-associating reactions. Gelification is induced, for example, for collagen by an increase in pH, for agarose by lowering the temperature, for alginate by addition of calcium.

It is further known, for example, from WO 00/37124, how to provide certain derivates of hyaluronic acid as a gel in which chondrocytes are dispersed. This gel is injected into patients to treat, inter alia, chondral and osteochondral damage, advantage being taken here of the fact that hyaluronic acid as such usually occurs in all mammalian species and is therefore generally well tolerated.

Furthermore, gels are known in which chitosan or derivates of chitosan are used as a base support material. WO 99/07416, for instance, discloses a gel which is based partly on chitosan and partly on a polyol and in which cells can be encapsulated. Here, advantage is taken of the fact that the composition gels in situ, triggered in fact by certain temperatures.

Apart from the injection or implantation of gels, another approach for treating cartilage damage currently involves either injecting cartilage cells as a suspension of free cells into a membrane-covered cartilage defect in a joint or introducing the cells initially into a support in vitro and then implanting them together with the support into the defect. In intervertebral disc defects, the cells have up to now only been injected directly, with the result, however, that there is no control of the whereabouts of the cells in the defect. Hitherto, two types of gels are found in clinical applications in the case of autologous chondrocyte transplantation in joints: collagen gels and fibrin gels, the latter being formed by an enzymatically catalyzed reaction. The former serves as a support for the cartilage cells, while fibrin is primarily used for sealing the repaired defect after introduction of the cells with or without support.

Fibrin gels have a number of disadvantages. They can turn very hard later and, as a result, damage the cartilage cells. Furthermore, fibrin gels are expensive, since they have to be prepared with the recombinant proteins thrombin and factor 13. A further disadvantage of fibrin gels is that fibrin itself can trigger inflammation reactions, and the gels have to be used at 37° C.

Collagen gels are generally well tolerated by the implanted cells; however, they have the disadvantage that they in part—i.e., depending on the preparation method—can shrink considerably and therefore actually cause failures during treatment, since they can fall out of the defect. Furthermore, there are also more recent findings that chondrocytes can die in collagen gels. Furthermore, collagen gels cannot be administered by injection because of high viscosity.

Particularly, in the treatment of intervertebral disc damage, there is a great need for alternative treatment methods and for materials to be used for this purpose. Intervertebral discs connect the vertebral bodies of the vertebral column to one another and provide the necessary mobility for bending and turning and counteract the compression caused by gravity when walking upright. Intervertebral discs consist of two parts, the outer Anulus fibrosus (fibrous ring) and the inner Nucleus pulposus (gelatinous center). The Anulus fibrosus consists of concentric layers of collagenous connective tissue fibers (outer zone) which gradually transition inward into fibrocartilage (inner zone). The Nucleus pulposus (intervertebral disc center) is a gelatinous tissue containing few cells and having a high water content. It acts to absorb shock like a water mattress. Histologically, the healthy intervertebral disc center is therefore essentially characterized by a low cell density and much extracellular matrix without a blood supply, lymphatic vessels, or innervation. The associated low intrinsic regeneration capacity leads to an increased susceptibility to degeneration of the intervertebral disc. Since intervertebral disc centers are not vascularized, access to regenerative cell populations is generally also not available after damage has been suffered.

Standard treatments are currently the removal of the prolapse or a nucleotomy, and the fusion of the vertebral bodies concerned. In both methods, however, severe consequences often occur. These include postnucleotomy syndrome and progressive neurological and clinical symptoms with the occurrence of a degeneration of the intervertebral discs in the adjacent segment.

Although the etiology and pathophysiology of intervertebral disc degeneration are not yet completely understood, it is already known that a series of different processes accompany the aging and degeneration of the intervertebral disc. Thus, cell vitality and proteoglycan content, more particularly, affect directly the biomechanics of the intervertebral disc, which is why a loss of cells and proteoglycan represents one of the most important causes of intervertebral disc degeneration.

Cell transplantation represents an alternative approach to the standard methods. Experiments in leporine and canine models showed that the treatment of a degenerated intervertebral disc with autologous intervertebral disc cells leads to revitalization of the Nucleus.

Against this background, it is an object of the present invention to provide an alternative to the approaches used up to now in the prior art in order that the disadvantages of the known procedures and materials may be overcome.

SUMMARY OF THE INVENTION

This and other objects is achieved according to the invention by an injectable biocompatible composition based on a polymeric support which comprises at least one hydrophilic polymer which is polymerizable in situ in mammals, wherein the at least one hydrophilic polymer is crosslinkable serum albumin or crosslinkable serum. It is especially preferred that the polymer is human albumin or human serum protein.

The composition according to the invention provides a material which is useful as a biocompatible and biodegradable hydrogel matrix and, in a preferred embodiment, can be loaded, for example, with appropriate adjuncts such as biologically or pharmaceutically active substances or cells. The material ensures the bioavailability or viability of the introduced adjuncts or cells after introduction to the desired site in patients, wherein the material can polymerize in situ at the same time without impairing the function or availability of adjuncts possibly present therein, such as living cells or biological or pharmaceutically active agents.

This is because the inventors have recognized in their experiments that serum albumin and serum proteins are very useful as a support material for the purposes of a use for treating defects/degeneration of cartilage or intervertebral discs. Advantage is here taken of the fact that serum albumin from blood serum and lymph of mammals is a carrier substance for substances occurring naturally in the body. Serum albumins are capable of binding a large number of different substances, such as, for example, metal ions (metals), fatty acids and amino acids, various proteins and drugs, which is why they are extremely biocompatible and elicit as good as no reactions in the body. It is further known that no molecular reactions with cartilage cells are elicited by albumin.

Serum proteins and/or albumin can be obtained from any mammal and be used for any mammal, although human and bovine serum albumin are preferred.

It is further advantageous in the composition according to the invention that the gel precursor can be handled at room temperature. The material can thus be stored separately from the particular adjuncts or cells to be introduced and be brought together with the adjuncts or cells just before the injection. The polymerization time is adjustable in that times between a few seconds and 2 minutes can be provided. Therefore, the adjuncts and/or cells become immediately anchored in the material, and so any undesired diffusion from the material is avoided.

In the present application, the terms "composition" and "material" are used for the claimed subject matter, with "composition" being used predominantly, but not exclusively, for the material which is still not polymerized, and "material" for the polymerized composition. Nevertheless, it will be appreciated that these terms cannot be completely separated from one another, since the composition and the material actually mean the same entity.

In the present application, the terms "composition" and "material" are used for the claimed subject matter, with "composition" being used predominantly, but not exclusively, for the material which is still not polymerized, and "material" for the polymerized composition. Nevertheless, it will be appreciated that these terms cannot be completely separated from one another, since the composition and the material actually mean the same entity.

Initial tests by the inventors have shown that crosslinked albumin dissolves after about 14 days. This is of great advantage, since, for example, cells have developed a pericellular matrix within this time period and have thus become incorporated in the surroundings. The present invention thus provides a material or a composition which has the advantage that it is liquid during the injection and hardens at the site to be treated and injected in a patient, in the intervertebral disc for example, to form a gel or hydrogel which, for example, prevents cells present in the composition from reemerging from the hole caused by the injection. Furthermore, the material is advantageously biodegradable.

It is provided in an embodiment when the albumin concentration in the completed, i.e., polymerized gel is from between about 5 to about 20, more particularly about 10 mg/ml gel.

According to the invention, it is provided in a preferred embodiment that, for example, living mammalian cells, more particularly human living cells, and also a pharmacological agent, a biologically active agent, or one or more or mixtures thereof are present in the composition.

Mammalian cells are understood to mean any cell which is derived or originates from a mammal, including, more particularly, human and animal cells. Such cells can, for example, be selected from skeletal muscle cells, more particularly chondrocytes, osteocytes, fibrochondrocytes, and also metabolism-regulating glandular cells, islet cells, melatonin-producing cells, progenitor cells and stem cells, more particularly mesenchymal stem cells, i.e., cells which are suitable and desired for the particular use of the composition or for the particular injection site.

The inventors were able to show in their studies that both chondrocytes and mesenchymal stem cells brought to differentiation into chondrocytes in the composition were viable in the composition. Thus, such compositions according to the invention which comprise these cells can, for example, be used advantageously for regenerating degenerated cartilage tissue and intervertebral discs.

Particularly mesenchymal stem cells have the advantage that, by resorting to these cells, even cases can be treated in which no autologous intervertebral disc tissue is available as a source of cells. Although it is preferred in an embodiment when autologous cell material is used according to the invention in the composition, donor cells, more particularly mesenchymal stem cells, can also be used. In their studies, the inventors were able to show that mesenchymal stem cells (also referred to as "MSC" below) were able to be isolated in a sufficient amount and at a high quality from all donors tested (over 100). Thus, adult mesenchymal stem cells represent an almost unlimited, expandable source of cells which is accessible without any problems for the surgeon via a puncture of the iliac crest and aspiration of bone marrow, and which can be differentiated in vitro into multiple cell types of the mesenchymal line, chondrogenic included.

Therefore, for the purposes of the present invention, either autologous or allogeneic mesenchymal stem cells, for example, can be isolated, expanded, and differentiated, for example, into chondrocytes, and also subsequently introduced into the composition. On the other hand, it is, however, also possible to introduce the mesenchymal stem cells directly into the composition, together with, for example, appropriate differentiation factors which then effect in situ appropriate differentiation.

The composition according to the invention which is loaded with the cells desired and suitable for the specific use has the advantage that support of the phenotype of the tissue to be regenerated can be achieved with them. In addition, de novo synthesis and the deposition of extracellular matrix can also be promoted, which is more particularly desirable for the treatment of intervertebral disc defects.

In addition, the compositions can also be used as a type of temporary cell depot and can, for this purpose, be loaded, for example, with cells which produce certain hormones, such as, for example, insulin, thryoxine, or melatonin. The cells present in the composition are injected at the desired site, after which the composition polymerizes in situ. The cells present in the composition are viable in the polymerized material, produce the respective hormones, and release them into the surroundings.

It can be further provided in another embodiment that appropriate cells are introduced with the composition into large wound areas, for example, the skin, liver, or spleen, in order to effect regeneration of the wounded tissue there.

The composition can, instead of or in addition to cells, also comprise one or more biologically or pharmaceutically active substances, or mixtures thereof.

"Biologically active substance" and "pharmaceutically active substance" shall herein denote any natural or synthetic substance which can have either a biological or pharmaceutical influence on cells or tissue, and can exert reactions on or in cells. This influence can be restricted to certain cells and certain conditions without the substance losing its biologically or pharmaceutically active denotation. The chemical constitution of the substances usable here is not restricted to a certain (compound) class, but can instead include any natural and synthetic substance which exerts inherently and/or in a modified form some action on biological cells.

It is thus especially preferred when, for example, antibiotics, anti-inflammtories, metabolism hormones, chondroprotectives, agents for gene therapy, growth hormones or differentiation and/or modulation factors, immunosuppressives, immunostimulatory substances, generally peptides, proteins, nucleic acids, organic active ingredients, hyaluronic acid, apoptosis-inducing actives, adhesion-mediating actives, receptor agonists and receptor antagonists, or mixtures thereof are used as biologically or pharmaceutically active substances. Proteins of the extracellular matrix, proteins of the cell surface, and also generally polysaccharides, lipids, antibodies, growth factors, sugars, lectins, carbohydrates, cytokines, DNA, RNA, siRNA, aptamers, and also binding—or action-relevant fragments thereof, and also disease-modifying osteoarthritis agents (DMOAs), or mixtures thereof can further be used. All the substances can be prepared synthetically or naturally occurring or originate from recombinant sources. "Disease-modifying osteoarthritis agents" are understood to mean a series of substances which are currently used as a medicament particularly in arthrosis—but now also in further autoimmune diseases—for alleviating pain and inflammation, and whose exact mechanism of action is still not comprehensively understood. Most of these substances comprise mixtures of glucosamine and chondroitin sulfate.

It is especially preferred in an embodiment when the biologically active substance is hyaluronic acid and is present in the gel at a final concentration of between about 1 to about 10 mg/ml gel, more particularly at about 4 mg/ml gel.

"Binding—or action-relevant fragments thereof" means parts or segments of the recited substances which, although possibly not the entire substance is used, do by themselves exert the same or virtually the same or at least a similar reaction or action on cells as the entire substance. Reaction can be understood to mean the mere binding of/to cells, but also the reaction subsequent to a binding in a cell to the binding, such as, for example, the triggering of certain reaction pathways in the cells which can lead to a production/release of certain substances by the cells, or, alternatively, to a transformation or differentiation of the cells.

Further examples include, however not exclusively, the following synthetic or natural or recombinant sources thereof: growth hormones, including human growth hormone and recombinant growth hormone (rhGH), bovine growth hormones, porcine growth hormones; growth-hormone—releasing hormones; interferons, including interferons alpha, beta, and gamma; interleukin-1; interleukin-2; insulin; insulin-like growth factor, including IGF-1; heparin; erythropoietin; somatostatin; somatotropin; protease inhibitors; adrenocorticotropin; prostaglandins; and also analogs, fragments, mimetics, or polyethylene glycol (PEG)-modified derivates of these compounds; or a combination thereof. It will be appreciated that all current (active) ingredients in the general area of therapy of diseases to be released in situ by supports/matrices come into consideration for application by the present invention, wherein it will be apparent in each case to a person skilled in the art that the (active) ingredient to be used or the cells to be used depend on the particular case to be treated.

It is preferred in an embodiment of the composition according to the invention when the serum albumin or the serum protein is functionalized by groups which are selected from maleimide, vinyl sulfone, acrylate, alkyl halide, azirine, pyridyl, thionitrobenzoic acid groups, or arylating groups.

"Functionalized" or functionalizing is understood here to mean any—completed—process in which the polymer—for example, by adding groups to the polymer—is given a function which it does not normally have.

The inventors were able to show in their experiments that good crosslinking of the polymer and, at the same time, the viability of cells or biofunctionality of substances can be achieved and ensured by functionalizing the polymer with maleimide groups.

The cells or substances to be optionally introduced into the composition are introduced by dispersion into the composition with the functionalized polymer which crosslinks with the cells.

The use of functionalized serum albumin or serum protein as an injectable, in situ polymerizable composition is neither disclosed nor suggested in the prior art.

The invention further provides for the use of serum albumin and/or serum protein for preparing an injectable biocompatible composition, more particularly the use of autologous serum albumin and/or serum protein.

The present use advantageously makes possible the provision of a composition which is outstandingly useful as an injectable, in situ polymerizable material in which, for example, cells and/or biologically or pharmaceutically active substances can also be additionally incorporated. This is because the composition ensures the survivability and the bioavailability of the adjuncts dispersed within, and is furthermore completely safe for and well tolerated by the patient to be treated, since the basic substance or the hydrophilic polymer, viz., albumin or serum protein, represents a substance which is regularly found in body fluids. After the injection into a patient at the site to be treated, the composition polymerizes; as a result, the material can mechanically support the concerned tissue to be treated and/or regenerate the tissue through the cells and/or substances present in the composition.

It is especially preferred when functionalized serum albumin or functionalized serum protein is used for preparing an injectable biocompatible composition, and preferably maleimide-functionalized serum albumin or maleimide-functionalized serum protein.

It is provided according to the invention that the composition is used for preparing biocompatible, degradable materials for use in pharmacology, veterinary and/or human medicine.

Thus, the present invention also relates to a method for treating cartilage disorders of a diseased or injured articular site in a mammal, said method comprising the steps of a) providing an effective amount of an injectable biocompatible composition based on a polymeric support which comprises at least one hydrophilic polymer, wherein the polymer is polymerizable in situ to form a gel, wherein the hydrophilic polymer is crosslinkable serum albumin or crosslinkable serum protein and wherein the serum albumin or the serum protein is functionalized by groups which are selected from maleimide, vinyl sulfone, acrylate, alkyl halide, azirine, pyridyl, thionitrobenzoic acid groups, or arylating groups, wherein the serum albumin or the serum protein is crosslinkable via the groups, and b) injecting the compositions into the articular site to be treated.

As mentioned above, the composition or rather the biocompatible material prepared therefrom is also useful as a constituent or as a whole in implantable devices or as an implant for use in the restoration, the reconstruction, and/or the replacement of tissues and/or organs, or as a drug release implant in mammals.

It is especially preferred when the composition is used for treating, replacing and/or for regenerating articular cartilage, intervertebral discs, bone tissue, tissue-building cells, and metabolism-regulating secretory cells.

The inventors were able to show in their studies that the composition according to the invention, loaded with cells, no tissue intolerance was elicited after injection and in situ polymerization. At the same time, the cells present in the composition were living. This shows that the present composition provides an outstanding biomaterial with which degenerated tissue can be regenerated again by provision of cells.

It will be appreciated that, depending on the tissue to be regenerated, appropriate cells and/or adjuncts are added to the composition. For instance, in a treatment of intervertebral disc damage, use can be made of chondrocytes or mesenchymal stem cells which can regenerate the degenerated intervertebral disc. On the other hand, the composition can, for example, also be used as a drug release system, in which case the composition is loaded with the desired and intended active ingredient/drug/pharmaceutical and injected into the patient. After polymerization of the composition in the patient, the active ingredient can be released from the polymerized composition, since this composition is biodegradable. Here, it is advantageous that a local administration can take place, and so systemic administrations which are a strain on the body can be avoided. It will be apparent to a person skilled in the art whether and which cells or adjuncts or biologically or pharmaceutically active substances can or must be added to the composition in order to ensure an optimal treatment approach.

The invention further provides a process for preparing an injectable biocompatible composition, comprising the following steps:
a) providing serum protein or serum albumin;
b) functionalizing with maleimide, vinyl sulfone, acrylate, alkyl halide, azirine, pyridyl, thionitrobenzoic acid, or arylating groups;
c) optionally adding mammalian cells and/or biologically or pharmacologically active substances; and
d) adding a crosslinker for crosslinking the serum or serum albumin functionalized in step b).

Crosslinkers which come into consideration include, for example, substances which carry SH groups, more particularly polymers, and, for example, dithio-PEG or SH-modified dextran, SH-modified polyvinyl alcohol, SH-modified polyvinylpyrrolidone, or SH-modified polyethylene glycol (SH-PEG).

The reaction chemistry of the process according to the invention is thus based, for example, in a preferred embodiment on the use of maleimide as a divalent conjugation molecule which becomes coupled to albumin on one side. In the actual crosslinking reaction, the second side of the albumin reacts with a double-sidedly thiolated polyethylene glycol (SH-PEG) which acts as a coupler between two maleimides attached to the albumin. The SH-PEG also serves as a spacer in order to create sufficient intervening space for water and small, diffusing molecules. In the cross-linking reaction, hyaluronic acid, for example, can then also be present, the very long chains of which are captured in the gel by the crosslinking reaction. Arising as a result is a physically stable gel conformation in which the hyaluronic acid can no longer escape from the gel by diffusion. Only after the biological degradation of the gel in situ is there release of degradation products, such as, inter alia and more particularly, maleate (malic acid)—and in the presence of hyaluronic acid—of hyaluronic acid fragments.

To prepare an embodiment of the gel according to the invention, a composition comprising albumin/hyaluronic acid/cell suspension is thus contacted with the crosslinker immediately before introduction into the site to be treated. For this purpose, the active components (albumin/optionally hyaluronic acid/cell suspension) are in a volume of, for example, 2 ml, and, for example, SH-PEG solution in a volume of, for example, 0.5 ml introduced into a double-chamber syringe and sent through a mixing chamber by depressing the plunger. The polymerization reaction then takes place in about 2 to 3 minutes. As a result, sufficient time advantageously remains for an even distribution of the gel mixture in the tissue.

Further advantages will be apparent from the description and the accompanying drawing.

It will be appreciated that the features mentioned above and the features still to be elucidated below are usable not only in the combinations specified in each case but also in other combinations or alone without departing from the scope of the present invention.

BRIEF DESCRIPTION OF THE DRAWINGS

Exemplary embodiments of the invention are illustrated in the drawing and are elucidated in more detail in the description below. In the drawing.

DESCRIPTION OF PREFERRED EMBODIMENTS

Example

Figure 1:
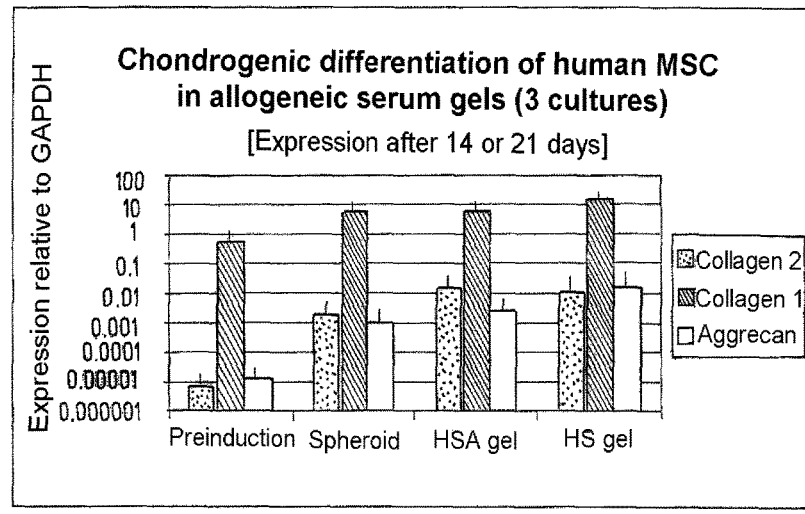
FIG. 1 shows a diagram for the analysis of the expression of certain marker genes after induction of chondrogenic differentiation of human stem cells.

Preparing Maleimide-modified Bovine Serum Albumin 250 mg of human serum albumin (Sigma-Aldrich, catalog number A1653) were dissolved in 5 ml of 1 M sodium borate (pH 8.2). To this, 75 µl of a 260 mM N-maleoyl-β-alanine (Sigma-Aldrich, catalog number 63285) solution in PBS/sodium borate (pH 8.2) (1:1) were added and incubated for 90 minutes at room temperature. 106 mg of 3-maleimidopropionic acid N-hydroxysuccinimide ester (SMP, Obiter Research, Urbana, Ill., USA) were dissolved in 950 µl of dimethylformamide (DMF). Insoluble material was separated by centrifugation. 500 µl of the supernatant were added to the albumin solution, which was subsequently incubated for 60 minutes at room temperature. Afterwards, 500 µl of 3 M sodium acetate (pH 4.7) were added and dialyzed three times against 1 liter of PBS on ice. The dialysate was subsequently concentrated by ultrafiltration (YM-3 membrane, Millipore) to a volume of 3.5 ml, filter-sterilized, and stored at −80° C.

Preparing Maleimide-modified Human Serum

75 µl of a 260 mM N-maleoyl-β-alanine (Sigma catalog number 63285) solution in PBS/1 M sodium borate (pH 8.2) (1:1) were added to 5 µl of human serum (AB-Pool, Tetec GmbH, Reutlingen) and incubated for 90 minutes at room temperature. Afterwards, 0.5 ml of 1 M sodium borate (pH 8.2) were added. To this, 500 µl of the SMP supernatant (example 1) were added and incubated for 60 minutes at room temperature. Afterwards, 500 µl of 3 M sodium acetate (pH 4.7) were added and dialyzed three times against 1 liter of PBS on ice. The dialysate was concentrated by ultrafiltration (YM-3 membrane, Millipore) to 3.5 ml. Insoluble material was separated by passage through the plug of a 1 ml pipette tip. The filtrate was filter-sterilized and stored at −80° C.

Preparing Maleimide-modified Bovine Serum Albumin 250 mg of BSA (Sigma-Aldrich, catalog number A7030) were dissolved in 5 ml of 1 M sodium borate (pH 8.2). 6 mg of N-maleoyl-β-alanine (Sigma-Aldrich, catalog number 63285) were added to the solution, and the solution was incubated for 2 hours at room temperature. In addition, 130 mg of N-hydroxysuccinimide were dissolved in 730 µl of acetonitrile. Afterwards, 96 mg of N-maleoyl-β-alanine were dissolved in 570 µl of the N-hydroxysuccinimide solution. To this solution, 80 µl of acetonitrile and 80 µl of diisopropylcarbodiimide were added. After a 5-minute incubation at room temperature, the batch was centrifuged for 5 minutes. The supernatant was added dropwise to the BSA solution with continuous stirring. After incubation for 45 minutes at room temperature, the batch was dialyzed four times against 500 ml of PBS on ice and subsequently concentrated by ultrafiltration to a volume of 4 ml.

Testing the Albumin Gels as a Support for Chondrocytes In Vitro

Experiments Carried Out—Cell Culture:

Chondrogenic differentiation of human mesenchymal stem cells in human serum gels and human serum albumin gels in comparison with standard methods (spheroid culture).

Procedure:

To prepare the gels or spheroids, human mesenchymal stem cells (P2 or P3) were used.

Preparation of Gels:

The MSCs were embedded at concentrations of 1 million or 5 million per milliliter of gel as follows:

|  | Human serum albumin | Human serum |
| --- | --- | --- |
| Add SPS to the plate | 34 µl | 24 µl |
| Cell pellet | 1 million | 1 million |
| Resuspend with medium | 83 µl | 88 µl |
| Mix with the gel material and into | 83 µl | 88 µl |
| Final volume | 200 µl | 200 µl |

After 5 minutes of polymerization at room temperature, the gels were overlaid with 500 µl of chondrogenic induction medium.

Preparation of Spheroids:

0.5 million cells were taken up in 20 µl of medium and carefully pipetted into a microwell plate as a single drop, subsequently incubated for 2-4 hours, and then overlaid with chondrogenic induction medium (500 µl).

Duration of Cultivation: 14-21 Days

The various batches were evaluated by gene expression analysis in comparison with the original cells prior to induction.

Result:

In both human gel materials, chondrogenic differentiation of the stem cells corresponding to the spheroid culture was induced (for this, see the diagram in FIG. 1). The gene expression of collagen 1 (gray bars), collagen 2 (black bars), and aggrecan (white bars) was investigated 14 or 21 days after induction. The expression of GAPDH (glyceraldehyde 3-phosphate dehydrogenase) served as the norm.

As is evident from the diagram, the analysis of the expression of the mentioned marker genes after induction of chondrogenic differentiation of human stem cells showed that the expression of collagen 2 and aggrecan is distinctly increased in the human serum albumin (HSA)—or human serum (HS)—gels. Thus, the expression is comparable to gene expression in the spheroid model. (Quantitative rt-PCR, expression normalized to GAPDH).

An observation of the differentiation process over a longer period of time (>14 days) was not possible, since the human HS and HSA gels were virtually completely degraded under induction conditions after 10-14 days in culture.

Testing the Albumin Gels as a Support for Chondrocytes In Vivo

Procedure:

1) Chondrocytes (*Sus scrofa*) and Gel (Cell Culture Room)

Before injection of the gel into the Scid mouse, a mixture of BSA7 gel and the porcine chondrocytes used was set up in the cell culture room.

To this end, 1 million porcine chondrocytes were centrifuged down in an Eppendorf vessel, and the pellet was resuspended in 400 µl of DMEM. Subsequently, 400 µl of BSA7 gel were added, and the solution was mixed by pipetting up and down two times. The gel was stored on ice for transport. 120 µl of SPS crosslinker were transferred to a separate Eppendorf cup and also stored on ice.

2) Mouse Experiment (Animal Facility)

In the animal facility, both components were mixed immediately before the injection into the mouse. To this end, the 120 µl of SPS crosslinker were initially drawn into a 5 ml syringe via a 0.6 mm needle, and a small air chamber was generated. Then, the 800 µl gel/cell mixture set up were drawn up via a 0.9 mm needle and thereby mixed with the crosslinker Subcutaneous injection took place immediately afterwards beneath the skin of the neck of the SCID mice anesthetized with ketanest (2 animals). During injection, a spherical gel formed.

The mice were housed as normal for 10 days and then sacrificed. The skin at the back was opened with one cut, and the gels were exposed. There were macroscopically no signs of tissue intolerance, such as inflammation and/or pus, to be observed.

Figures 2A, 2B:
FIG. 2a, b show Giemsa-stained porcine chondrocytes in the albumin gel.

The gel pieces were then removed and fixed overnight at 4° C. in a 10% formalin solution, and then stored at 4° C. in a 1% formalin solution until they were used in histology. Frozen sections with a thickness of about 50 µm were made and freshly stained (Giemsa, DAPI) for the histology. The wet sections were covered immediately with a coverslip and examined immediately afterwards under the microscope (see FIG. 2). The gels had a foamy and porous organization. All detectable cells were living. Some of the chondrocytes were found to be proliferating and surrounded by a halo of extracellular matrix. At the periphery of the implants, some smaller fibroblastoid cells were detectable, probably migrated connective tissue cells from the mouse.

What is claimed is:

1. Method for treating cartilage disorders of a diseased or injured articular site in a mammal, said method comprising the steps of providing an injectable biocompatible composition based on a polymeric support which polymeric support comprises a hydrophilic polymer, wherein the hydrophilic polymer is polymerizable in situ to form a gel, wherein the hydrophilic polymer is serum albumin and wherein the serum albumin is functionalized by maleimide groups, wherein the serum albumin is cross-linked in situ via the groups via a thiol reaction, and injecting the composition into the articular site to be treated.

2. The method as claimed in claim 1, wherein the composition is used for replacing and/or for regenerating articular cartilage or intervertebral discs.

3. The method as claimed in claim 1, wherein the composition is used for introducing chondrocytes and/or mesenchymal stem cells into the articular site to be treated.

4. The method as claimed in claim 1, wherein the composition further comprises chondrocytes and/or mesenchymal stem cells.

5. The method as claimed in claim 1, wherein the composition further comprises a pharmacological agent, the pharmacological agent being selected from at least one of the following: an antibiotic, an anti-inflammatory, a metabolism hormone, chondroprotectives, agents for gene therapy, growth hormones, differentiation or modulation factors, immunosuppressives, immunostimulatory substances, DMOAs, nucleic acids, apoptosis-inducing actives, adhesion-mediating actives, receptor agonists and receptor antagonists, or mixtures thereof.

6. The method as claimed in claim 1, wherein the composition further comprises hyaluronic acid.

7. The method as claimed in claim 1, wherein the composition further comprises a SH group-containing crosslinker.

8. The method as claimed in claim 7, wherein the SH group-containing crosslinker is selected from SH-modified dextran, SH-modified polyvinyl alcohol, SH-modified polyvinylpyrrolidone, or SH-modified polyethylene glycol.

9. Method for treating cartilage disorders of a diseased or injured articular site in a mammal, said method comprising the steps of providing an injectable biocompatible composition based on a polymeric support which polymeric support comprises a hydrophilic polymer, wherein the hydrophilic polymer is polymerizable in situ to form a gel, wherein the hydrophilic polymer is serum albumin or serum protein and wherein the serum albumin or serum protein is functionalized by maleimide, wherein the serum albumin or serum protein is cross-linked in situ via the groups via a thiol reaction, and wherein the composition further comprises a SH group-containing crosslinker, and injecting the composition into the articular site to be treated.

* * * * *